(12) United States Patent
Kulik et al.

(10) Patent No.: US 11,028,033 B2
(45) Date of Patent: Jun. 8, 2021

(54) METHOD FOR PRODUCING TERPENE ALDEHYDES AND TERPENE KETONES

(71) Applicant: SYMRISE AG, Holzminden (DE)

(72) Inventors: Anna Kulik, Rostock (DE); Reinhard Eckelt, Rostock (DE); Angela Köckritz, Berline (DE); Katja Neubauer, Rostock (DE)

(73) Assignee: SYMRISE AG, Holxminden (DE)

( * ) Notice: Subject to any disclaimer, the term of this patent is extended or adjusted under 35 U.S.C. 154(b) by 0 days.

(21) Appl. No.: 16/642,188

(22) PCT Filed: Aug. 26, 2017

(86) PCT No.: PCT/EP2017/071478
§ 371 (c)(1),
(2) Date: Feb. 26, 2020

(87) PCT Pub. No.: WO2019/042520
PCT Pub. Date: Mar. 7, 2019

(65) Prior Publication Data
US 2020/0181052 A1 Jun. 11, 2020

(51) Int. Cl.
*C07C 45/29* (2006.01)
(52) U.S. Cl.
CPC .................... *C07C 45/29* (2013.01)
(58) Field of Classification Search
CPC ....................................... C07C 45/29
See application file for complete search history.

(56) References Cited

U.S. PATENT DOCUMENTS 7,468,463 B2 * 12/2008 Johann .................. C07C 45/002
568/338
9,790,157 B2 * 10/2017 Limburg .............. B01J 31/0202

FOREIGN PATENT DOCUMENTS

WO    2019042520 A1    8/2017

OTHER PUBLICATIONS

Csjernyik et al. Efficient Ruthenium-Catalyzed Aerobic Oxidation of Alcohols Using a Blomometic Coupled Catalytic System. Journal of Organic Chemistry, vol. 62, 1657-1662. (Year: 2002).*
Kantam et al. Ruthenium/magnesium-lanthanum mixed oxide: An efficient reusable catalyst for oxidation of alcohols by using molecular oxidation. Journal of Molecular Catalysis A: Chemical, vol. 39, 1-7. (Year: 2012).*
PCT/EP2017/071478; PCT Search Report and Written Opinion; dated May 24, 2018; 13 pages.
Costa, V. V. et al., "Aerobic oxidation of monoterpenic alcohols catalyzed by ruthenium hydroxide supported on silica-coated magnetic nanoparticles", Journal of Catalysis, 2011, vol. 282, pp. 209-214.

* cited by examiner

*Primary Examiner* — Sikarl A Witherspoon
(74) *Attorney, Agent, or Firm* — Michael P. Byrne; Wolter Van Dyke Davis, PLLC

(57) ABSTRACT

The invention relates to a method for producing terpene aldehydes and terpene ketones by oxidatively dehydrogenating the corresponding terpene alcohols, comprising or consisting of the following steps: (a) providing terpene alcohols or terpene-alcohol-containing reactants; (b) bringing the starting substances from step (a) in contact with a heterogeneous ruthenium catalyst; (c) heating the mixture from step (b) to at least 150° C. in the presence of oxygen; optionally (d) separating the terpene aldehydes or terpene ketones from the obtained reaction mixture.

18 Claims, No Drawings

METHOD FOR PRODUCING TERPENE ALDEHYDES AND TERPENE KETONES

CROSS-REFERENCE TO RELATED APPLICATION

This application is a national stage entry of and claims priority to PCT/EP2017/071478, filed Aug. 26, 2017, which is hereby incorporated by reference in its entirety.

FIELD OF THE INVENTION

The invention is in the field of heterogeneous catalysis and relates to a method for producing terpene aldehydes and terpene ketones from terpene alcohols by oxidative dehydrogenation.

BACKGROUND OF THE INVENTION

Terpene ketones, especially menthone, are used in perfumery to create specific mint notes in perfume compositions. The reaction can be exemplified by the following scheme:

Scheme 1
Reaction of (-)-menthol to give (-)-menthone and (+)-isomenthone

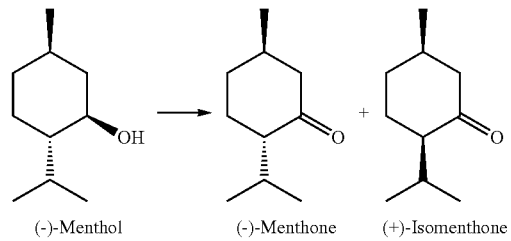

(-)-Menthol     (-)-Menthone     (+)-Isomenthone

Numerous methods are known from the prior art with which, for example, menthone or mixtures of menthone and isomenthone can be obtained starting from menthol. The more outdated methods include non-catalytic methods in which problematic oxidizing agents, from a toxicological and ecological point of view, such as dichromate, permanganate or chlorine dioxide, are used in stoichiometric amounts [FROLOVA ET AL, Chem. Natural Comp. 44, pp. 724 ff. (2008)].

The aerobic catalytic oxidation of secondary alcohols to ketones has already been carried out with various heterogeneous catalysts. Gold, ruthenium, palladium, rhodium, iron, copper or vanadium, for example, have been used as active metals in suitable oxidation stages and integrated in suitable materials; reactions in the field of fine chemical syntheses were mostly conducted in discontinuous mode in the liquid phase (cf. RSC Green Chemistry Series (CARDONA ET AL, Volume 28: *Transition Metal Catalysis in Aerobic Alcohol Oxidation*, The Royal Society of Chemistry, Cambridge, UK, 2015).

$Ru(OH)_x$ or $RuO_x \cdot xH_2O$, which comprise $Ru'''^+OH$ species, are highly active catalysts for aerobic oxidative dehydrogenation of alcohols. The prerequisite for good catalytic activity is the highly dispersed application of the active species on a suitable support material, for example aluminum oxide. However, the supported catalyst obtained in this way has so far been used predominantly in the liquid phase in batch reactors [e.g. YAMAGUCHI ET AL, Angew. Chem 114 (2002) 4720; YAMAGUCHI ET AL, Chem. Eur. J. 9 (2003) 4353; YAMAGUCHI ET AL, Top. Catal. 57 (2014) 1196; PAGLIARO ET AL, Chem. Soc. Rev. 34 (2005) 837)].

$Ru/MgO-La_2O_2$ mixed oxides were also used for the aerobic oxidation of activated alcohols in toluene at 80° C. [KANTAM ET AL, J. Mol. Catal. A: Chem. 359, 1 (2012)]. $Ru/CaO-ZrO_2$ was also investigated, but no cycloaliphatic alcohol was used as substrate [YASUEDA ET AL, J. Mol. Catal. A Chem. 323, 7 (2010)]. RuHAP (HAP=hydroxyapatite) is suitable as catalyst for the oxidation of benzyl alcohol and 1-phenylethanol [KIM ET AL, Bull. Korean Chem Soc. 34, 221 (2013)]. Using $Ru/CeO_2$, benzyl alcohol was oxidized to benzaldehyde [WADA ET AL, Catal. Surv. Asia 15, 1 (2011)].

The addition of further oxidation-active oxidic metal species has a favorable effect on the conversion of primary alcohols and the yield of aldehydes. For instance, $Ru/TiO_2$ or $Ru/ZrO_2$, which had been doped with a second oxide, were investigated [KÖCKRITZ ET AL, J. Mol. Catal. A: Chem. 246, 85 (2006)]. A further improvement of the activity of this type of catalyst is achieved if the oxidic metal species, especially RuMnCe, have been distributed as nanoparticles onto $CeO_2$ [CHECINSKI ET AL, Appl. Catal. A: Gen. 366, 212 (2009)]. The oxidation of various primary and secondary alcohols to aldehydes and ketones was particularly successful in the presence of RuMnMn species on hydrotalcite [EBITANI ET AL, Angew. Chem. Int. Ed. 44, 3423 (2005)].

Activated carbon is also suitable as a support material for ruthenium catalysts for the oxidation of primary and secondary alcohols in organic solvents, but terpenes were not investigated and also no information was given on the active oxidation state of ruthenium [MORI ET AL, Chem. Comm. 5159 (2009)].

$Ru(OH)_x/Al_2O_3$ is also a suitable catalyst for a continuous process in the liquid phase using a solvent, but only alcohols activated by aromatics or heteroaromatics were used as substrates (MANNEL ET AL, Org. Process Res. Dev. 18, 1503 (2014)]

Overall, terpenes are rarely described as reactants for such reactions. Menthol is also a terpene alcohol that is difficult to oxidize. The alcoholic OH group is not activated and is also in the equatorial position. Thus, reactions are only known from the prior art which proceed in the liquid phase at temperatures significantly below 150° C. For instance, oxidation of menthol using $Ru(OH)_x/Fe_2O_3@SiO_2$ at 10 atmospheres oxygen pressure was only possible with 17% conversion and yield of menthone at 120° C. (COSTA ET AL, J. Catal. 282, 209 (2011)]. Using $Ru/CeO_2$ in toluene at 110° C., a yield of menthone of only 15% could be achieved [VOCANSON ET AL, Synth. Comm. 28, 2577 (1998)].

Other batch methods for producing menthone use thymol as reactant, which is subjected to partial hydrogenation over Pd catalysts in autoclaves at 175° C. (U.S. Pat. No. 3,124, 614), or isopulegol is converted to menthone on homogeneous Ru dihydrido phosphine or Ir dihydrido phosphine catalysts via a hydrogenation/dehydrogenation sequence (EP 2706054 A1).

The continuous non-oxidative dehydrogenation of menthol to menthone is possible in the gas phase on Cu/Zn or Cu chromite catalysts (DE 4236111 A1) or on $ZnO/CaCO_3$ catalysts (WO 2005 085160 A1), although preference is given to operating either at reduced pressure, which requires an equipment upgrade, or temperatures significantly above 300° C. are required, which favor the formation of undesirable by-products.

There is no continuous oxidative dehydrogenation process for the synthesis of terpene aldehydes or terpene ketones in general, and menthone in particular, in the gas phase. The specific object of the present invention was therefore to remedy this and to provide a method which is characterized in that at the same time
- good yields of a terpene aldehyde or terpene ketone in general and menthone/isomenthone mixtures in particular are obtained,
- there is no racemization at chiral centers,
- no solvent has to be used and removed,
- no removal of the catalyst is required,
- no operation under reduced pressure is necessary,
- the catalyst used allows operation at those temperatures at which by-product formation is relatively low,
- no leaching of the active metals into the product occurs in the gas phase, and
- a quality is obtained which is suitable for the perfume industry, i.e. the reaction product should not contain any olfactorily objectionable by-products.

DESCRIPTION OF THE INVENTION

The invention provides a method for producing terpene aldehydes and terpene ketones by oxidative dehydrogenation of the corresponding terpene alcohols, comprising or consisting of the following steps:

(a) providing terpene alcohols or terpene alcohol-containing reactants;

(b) bringing the starting materials of step (a) into contact with a heterogeneous ruthenium catalyst;

(c) heating the mixture of step (b) to at least 150° C. in the presence of oxygen; and optionally (d) separating the terpene aldehyde or terpene ketone from the resulting reaction mixture.

Surprisingly, it has been found that the requirement profile described at the outset is met in full by the method according to the invention: the terpene aldehydes or terpene ketones are obtained in high yields and with high selectivities which are significantly above those which were previously achievable according to the prior art. Neither did solvent have to be used, nor was there a need to remove the catalyst in a complex manner; the method also does not require reduced pressure. The temperature range to be maintained is so low that there is no appreciable by-product formation, meaning that qualities are obtained which meet the stringent requirements in the perfume industry.

Terpene Alcohols

In principle, the method according to the invention can be applied to all terpene alcohols. Examples of suitable terpene alcohols include borneols and fenchols, and in particular carveol, citronellol, cuminic alcohol, dihydrocarveol, farnesol, geraniol, nerol, perillyl alcohol, phytol and rhodinol and mixtures thereof. Menthol is preferably used in the context of the method according to the invention, which is converted to menthone or a mixture of menthone and isomenthone.

It is possible to use the terpene alcohols as individual substances. Mixtures of various terpene alcohols can also be converted, or natural product extracts having a content of these terpene alcohols in addition to other components.

Catalysts

In accordance with the present invention, heterogeneous ruthenium catalysts are used, which preferably have an oxidation state greater than zero. These catalysts can also have other catalytically active species, in particular other metal oxides. These can be selected from the group comprising cerium oxides, copper oxides, iron oxides, manganese oxides, cobalt oxides, molybdenum oxides, silver oxides and mixtures thereof. The following oxides are particularly preferred examples: $CeO_2$, $CuO$, $Cu_2O$, $Fe_2O_3$, $Fe_3O_4$, $MnO$, $MnO_2$, $Mn_2O_3$, $Mn_3O_4$, $Co_3O_4$, $CoO$, $MoO_3$, $AgO$, $Ag_2O$ and mixtures thereof. Doping, for example in amounts of about 10 to about 50% by weight, based on the amount of ruthenium, results in a significant increase in the catalyst activity.

In the context of the present invention, catalysts used are especially those in which the catalytically active species are applied to a support material. In this case, it is advantageous to apply these oxidized metal species—based both on ruthenium and on the other metals—to the support in a very finely divided form. Particular preference is given to carrying out the invention when the catalyst support itself consists of a material which is catalytically active for oxidations. The active catalyst is produced using wet chemical methods such as impregnation, impregnation to the onset of moisture, precipitation or co-precipitation. The metals to be introduced in the catalyst synthesis are used in the form of suitable precursors, for example as metal chlorides, metal nitrates or metal acetates. In order to be able to be used according to the invention in a continuous reactor, the crude catalyst mass is then subjected to shaping such as extrusion or pelletization and thermal treatment. The supports are preferably oxidic materials which are selected from the group comprising cerium oxide, aluminum oxide, zirconium oxide, titanium oxide, silicon oxide, silica, iron oxide, manganese oxide, niobium oxide, aluminosilicate, hydrotalcite, hydroxyapatite and mixtures thereof. Alternatively, activated carbon can also serve as a support.

The concentration of ruthenium or the mixture of ruthenium and other metals in their respective oxidic form on the support material can be between approximately 0.1 and approximately 10% by weight and preferably between approximately 0.5 and approximately 5% by weight.

Method

In accordance with the invention, continuous tubular reactors are used for the oxidative dehydrogenation of menthol. In this case, the catalyst can come into contact with the reactant in a fixed bed or fluidized bed. The design of the reaction plant according to the invention also includes tube bundle reactors.

Gaseous reactants flow through the catalyst introduced into the reactor. These reactants consist of gaseous menthol and an oxygen-containing gas. The oxygen-containing gas is supplied at suitable concentrations by mass flow controllers. The concentration of oxygen in the oxygen-containing gas is at least 0.1%. The terpene alcohol is supplied by a pump and conversion into the gas phase is carried out by conventional evaporator designs.

The method according to the invention requires a minimum temperature of 150° C. to ensure that the reaction proceeds in the gas phase, since this is critical for conversions and selectivity. Otherwise, the preferred temperature range is 150 to approximately 350° C., preferably approximately 180 to approximately 320° C. and especially 250 to approximately 300° C.

By setting the optimum temperature and residence time or GHSV (gas hourly space velocity), the yield and selectivity of, for example, the desired menthone/isomenthone mixture can be maximized. This can be seen as an advantage of this continuous process according to the invention.

It is further preferred to carry out the reaction in a reactor through which a gas stream flows continuously, said gas stream comprising the terpene alcohol, preferably menthol, and an oxygen-containing gas and optionally an inert gas when entering the reactor. In this case, the oxygen-containing gas preferably comprises at least 0.1% by volume oxygen, based on the total volume of the oxygen-containing gas, determined at 20° C. and 1013.25 hPa.

A further preferred embodiment of the method according to the invention also consists in that
(ii) the flow rate of the gas stream based on the volume of the heterogeneous catalyst (gas hourly space velocity GHSV) is about 100 $h^{-1}$ to about 5000 $h^{-1}$, preferably about 200 $h^{-1}$ to about 1000 $h^{-1}$ and/or
(ii) the concentration of terpene alcohol in the gas stream entering the reactor is about 1 mol % to about 15 mol %, preferably about 3 mol % to about 10 mol %.

Suitable residence times are in the range of τ=1-20 s. At the outlet of the reactor, the gaseous product mixture is condensed and subjected to a gas/liquid separation. The liquid product mixture can then be purified by distillation.

The method can be carried out either batchwise or preferably continuously.

EXAMPLES

Examples 1 to 9

General description of the apparatus used and the reaction regime

The continuous tubular reactor apparatus used consisted of a saturator, thermostat, gas lines, gas metering and control with digital MFCs, a tubular reactor with oven, one sample collection vessel temperature-controlled in an oil bath (filled with 6 mL of o-xylene) for high boilers and one sample collection vessel cooled in a cryostat for low boilers and several heaters with control elements and thermocouples.

To carry out the tests, the stainless steel tubular reactor was first filled with the previously granulated catalyst (3 mL). The saturator filled with menthol was then immersed in the thermostat solution, which was heated to the desired temperature (usually 120° C.). With the exception of the gas line to the saturator, the temperature of all other lines was set to 200° C. by heaters (heating bands) with thermocouples and control devices and kept constant. During the heating phase, the entire test apparatus was purged with $N_2$ via a gas line passing the saturator. A gas mixture of 5% by volume $O_2$/Ar (30 mL/min) was then passed into the saturator, which was temperature-controlled at 120° C., after the $N_2$ purge gas supply had been closed. The reaction was started by opening the gas valve from the saturator to the reactor. In order to prevent the unreacted menthol from crystallizing out (m.p.: 41-45° C.) at the reactor outlet, the gas line from the reactor outlet to the collection vessel was additionally heated to 100° C. In addition, the sample vessel with 6 mL of o-xylene as a collecting solution was heated to 60° C. with the aid of a temperature-controlled oil bath during the entire reaction time. A cold trap for collecting any more volatile products was located directly downstream of the actual sampling point. After the reaction was complete, the valve from the saturator to the reactor was closed and the system was purged with $N_2$. Then, all other control elements for gas metering and temperature control were switched off.

To determine the menthol consumption during the reaction, the saturator was removed after each test and weighed.

The total reaction time per temperature was always 3 hours, with hourly sampling. The tests were carried out under the following conditions:
3 mL of catalyst,
5 mol % menthol in the gas stream,
30 mL/min 5% by volume $O_2$/Ar,
Catalysts used:
[a]: Ru/C,
[b]: 0.2% Ru/$CeO_2$,
[c]: 0.2-1.0/1.2/1.6% RuMnCe/$CeO_2$,
wherein catalysts [a] and [b] are commercial products and catalyst [c] was obtained according to the following standard procedure:

To a suspension of 4.46 g of $CeO_2$ in 100 mL of deionized water was added a solution of 23.4 mg of $RuCl_3 \cdot H_2O$, 260.6 mg of $Mn(NO_3)_2 \cdot 4H_2O$ and 225.4 mg of $Ce(NO_3)_3 \cdot 6H_2O$ in 20 mL of water. Then, with the aid of a syringe pump, a solution of 415.2 mg of NaOH and 314.4 mg of $Na_2CO_3$ in 8 mL of water was continuously added dropwise over a period of 5 h while stirring the suspension. After the addition was complete, the reaction suspension was heated to 65° C. and stirred for 18 h. The solid was removed by centrifugation, washed three times with 20 mL of water each time, and dried overnight at 90° C. in a drying cabinet. The active components Ru, Mn and Ce are present on the support as oxides and/or hydroxides.

Observed conversions and yields are shown in Table 1 below.

TABLE 1

Conversions and yields

| Ex. | Ru content | T [° C.] | $X_{OL}$ [mol %] | $Y_{ON}$ [mol %] | $Y_{ISO}$ [mol %] | $Y_{NP}$ [mol %] | $S_{ON}$ [%] | $S_{ISO}$ [%] |
|---|---|---|---|---|---|---|---|---|
| 1 | 5[a] | 300 | 99 | 4 | 2 | 59 | 4 | 2 |
| 2 | 0.2[b] | 300 | 92 | 31 | 22 | 11 | 34 | 24 |
| 3 | 0.2[b] | 350 | 93 | 31 | 23 | 10 | 33 | 25 |
| 4 | 0.2[c] | 300 | 52 | 20 | 17 | 4 | 39 | 32 |
| 5 | 0.2[c] | 350 | 68 | 27 | 23 | 6 | 40 | 34 |
| 6 | 0.5[c] | 300 | 94 | 38 | 26 | 5 | 40 | 28 |
| 7 | 0.5[c] | 350 | 96 | 37 | 27 | 5 | 38 | 28 |
| 8 | 1.0[c] | 300 | 92 | 40 | 28 | 6 | 43 | 31 |
| 9 | 1.0[c] | 350 | 93 | 40 | 29 | 9 | 42 | 32 |

Key:
$X_{OL}$ = conversion of menthol in mol %
$Y_{ON}$ = yield of menthone in MOL %
$Y_{ISO}$ = yield of isomenthone in mol %
$S_{ON}$ = selectivity for menthone
$S_{ISO}$ = selectivity for isomenthone

The invention claimed is:
1. A method for producing terpene ketones by oxidative dehydrogenation of the corresponding terpene alcohols, the method comprising:
  bringing starting materials comprising terpene alcohols or terpene alcohol-containing reactants into contact with a heterogeneous ruthenium catalyst to form a mixture;
  heating the mixture at a temperature of about 180 to about 320° in the presence of oxygen to form a reaction mixture; and optionally
  separating the terpene ketones from the resulting reaction mixture,
  wherein a reaction to form the reaction mixture is carried out in a reactor through which a gas stream flows continuously, said gas stream comprising at least one terpene alcohol and an oxygen-containing gas and optionally an inert gas when entering the reactor.

2. The method as claimed in claim 1, wherein the starting materials comprise menthol.

3. The method as claimed in claim 1, wherein the heterogeneous ruthenium catalyst comprises one or more metal oxides.

4. The method as claimed in claim 3, wherein the one or more metal oxides are selected from the group comprising cerium oxides, copper oxides, iron oxides, manganese oxides, cobalt oxides, molybdenum oxides, silver oxides, and mixtures thereof.

5. The method as claimed in claim 3 wherein the one or more metal oxides are selected from the group comprising $CeO_2$, $CuO$, $Cu_2O$, $Fe_2O_3$, $Fe_3O_4$, $MnO$, $MnO_2$, $Mn_2O_3$, $Mn_3O_4$, $Co_3O_4$, $CoO$, $MoO_3$, $AgO$, $Ag_2O$, and mixtures thereof.

6. The method as claimed in claim 1, wherein the heterogeneous ruthenium catalyst comprises catalytically active species that are applied to a support material.

7. The method as claimed in claim 6 wherein the support material is also catalytically active.

8. The method as claimed in claim 6, wherein the support material is an oxidic support material.

9. The method as claimed in claim 6, wherein the support material is selected from the group comprising cerium oxide, aluminum oxide, zirconium oxide, titanium oxide, silicon oxide, silica, iron oxide, manganese oxide, niobium oxide, aluminosilicate, hydrotalcite, hydroxyapatite, and mixtures thereof.

10. The method as claimed in claim 6, wherein the support material comprises activated carbon.

11. The method as claimed in claim 6, wherein a concentration of ruthenium on the support material is between approximately 0.1 and approximately 10% by weight.

12. The method as claimed in claim 1, wherein the oxygen-containing gas comprises at least 0.1% by volume oxygen, based on the total volume of the oxygen-containing gas, determined at 20° C. and 1013.25 hPa.

13. The method as claimed in claim 1, wherein
(i) the flow rate of the gas stream based on the volume of the heterogeneous catalyst (gas hourly space velocity GHSV) is about 100 h-1 to about 5000 h-1, and/or
(ii) the concentration of terpene alcohol in the gas stream entering the reactor is about 1 mol % to about 15 mol %.

14. The method as claimed in claim 13, wherein
(i) the flow rate of the gas stream based on the volume of the heterogeneous catalyst (gas hourly space velocity GHSV) is about 200 h-1 to about 1000 h-1, and/or
(ii) the concentration of terpene alcohol in the gas stream entering the reactor is about 3 mol % to about 10 mol %.

15. The method as claimed in claim 6, wherein a concentration of ruthenium on the support material is between approximately 0.5 and approximately 5% by weight.

16. The method as claimed in claim 1, wherein a reaction to form the reaction mixture is carried out at a temperature in the range of approximately 250 to approximately 300° C.

17. A method for producing terpene aldehydes and terpene ketones by oxidative dehydrogenation of the corresponding terpene alcohols, the method comprising:
bringing starting materials comprising terpene alcohols or terpene alcohol-containing reactants into contact with a heterogeneous ruthenium catalyst of type RuMnCe/$CeO_2$;
heating the mixture to at least 150° C. in the presence of oxygen to form a reaction mixture; and optionally
separating the terpene aldehydes or terpene ketones from the resulting reaction mixture.

18. A method for producing terpene aldehydes and terpene ketones by oxidative dehydrogenation of the corresponding terpene alcohols, the method comprising:
bringing starting materials comprising menthol or a menthol-containing reactant into contact with a heterogeneous ruthenium catalyst to form a mixture;
heating the mixture to at least 150° C. in the presence of oxygen to form a reaction mixture; and optionally
separating the menthone from the resulting reaction mixture.

* * * * *